United States Patent [19]

Bischoff et al.

[11] 4,158,694
[45] Jun. 19, 1979

[54] AUTOMATED APPARATUS FOR TESTING SUSTAINED RELEASE DRUGS

[75] Inventors: Dennis E. Bischoff; Gary R. Dickinson; Michael E. Hinshaw; Robert M. Brooker, all of Indianapolis, Ind.

[73] Assignee: The Dow Chemical Company, Midland, Mich.

[21] Appl. No.: 891,663

[22] Filed: Mar. 30, 1978

[51] Int. Cl.$^2$ .......................... G01N 1/10; G01N 1/14
[52] U.S. Cl. ...................................... 422/81; 422/103
[58] Field of Search ............... 23/230 R; 422/81, 103; 364/497, 499

[56] References Cited

U.S. PATENT DOCUMENTS

| | | | |
|---|---|---|---|
| 3,223,486 | 12/1965 | Holl, Jr. et al. | 23/253 |
| 3,540,700 | 11/1970 | Freedman | 259/3 |
| 3,614,434 | 10/1971 | Horwitz et al. | 250/71.5 |
| 3,647,390 | 3/1972 | Kubodera | 23/259 |
| 3,742,190 | 6/1973 | Giani et al. | 219/389 |
| 3,787,185 | 1/1974 | Rohrbaugh | 23/253 R |
| 3,881,872 | 5/1975 | Naono | 23/253 R |
| 3,933,436 | 1/1976 | Naono | 23/253 R |

*Primary Examiner*—R. E. Serwin
*Attorney, Agent, or Firm*—James W. Ambrosius

[57] ABSTRACT

An automated apparatus for testing a sustained release drug according to a preselected program having a movable dissolution chamber, a first flow path connecting said chamber to a buffer reservoir, a second flow path connecting said chamber to a fluid collection reservoir and a third flow path connecting said chamber to a wash reservoir, and programming means for activating fluid flows between said reservoirs and said dissolution chamber in accordance with a preselected program.

3 Claims, 3 Drawing Figures

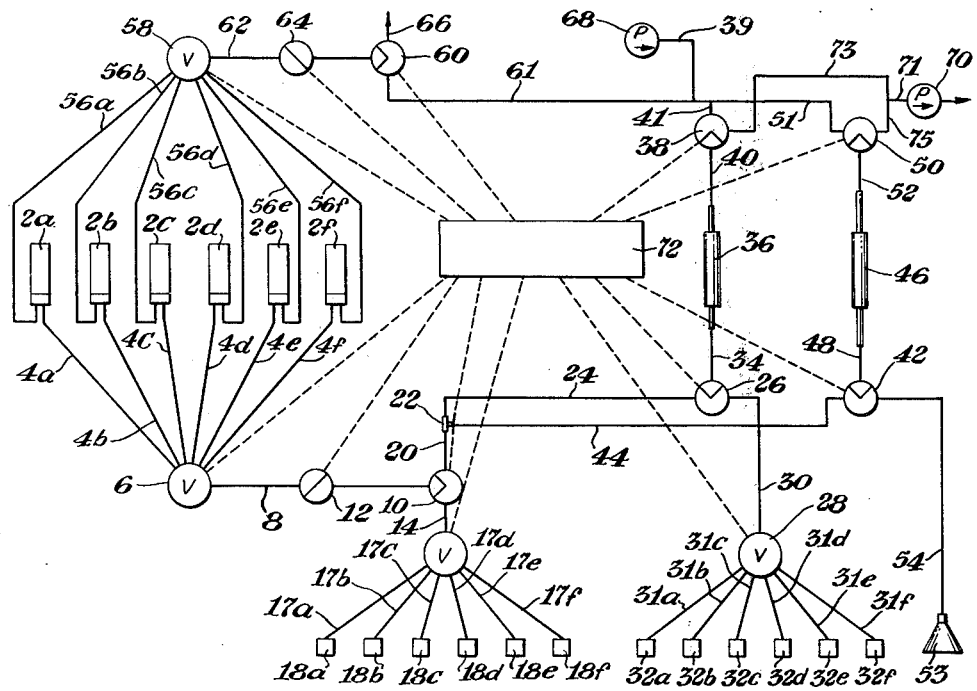

AUTOMATED APPARATUS FOR TESTING SUSTAINED RELEASE DRUGS

FIELD OF THE INVENTION

This invention relates to an automated apparatus for testing sustained release drugs.

BACKGROUND OF THE INVENTION

In testing a sustained release drug, a capsule, pellet, tablet or other form of the pharmaceutical product is exposed for a predetermined and reproducible time period to a selected solvent having a controlled pH. At the end of the exposure period, the solvent is separated from undissolved residue, and a new solvent with an increased pH is added to the residue. After several such solvent changes, the solutions are assayed, and the percentages of dissolution are determined. A typical device used in carrying out the above procedure is shown in U.S. Pat. No. 3,742,190.

Current methods require that an operator be present to change and collect the used solvents for assay. Although more than one sample may be run simultaneously, the manual procedure is still time consuming.

SUMMARY OF THE INVENTION

The present invention relates to an automated apparatus which carries out the testing of a sustained release product according to a preselected program. The apparatus consists of at least one dissolution chamber having means for circulating a buffer liquid and wash therethrough; an agitating means contacting the contents of the dissolution chamber or for moving the dissolution chamber during operation; a first flow path connecting said dissolution chamber and a buffer reservoir so constructed that a measured quantity of buffer may be introduced into the dissolution chamber; a second flow path to empty the buffer from the dissolution chamber into a fluid collection reservoir; a third flow path connecting the dissolution chamber to a wash reservoir so constructed that a measured quantity of wash liquid may be introduced into the dissolution chamber; valving means for selectively activating and deactivating said first, second, and third flow paths; and programming means for selectively operating the valving means whereby said first, second, and third flow paths are sequentially activated and deactivated according to a preselected program wherein the dissolution chamber is filled with buffer, agitated, emptied of buffer, and rinsed.

The agitating means includes conventional devices for stirring liquids such as for example mechanical stirrers and magnetic stirrers. In addition, means for moving the entire dissolution chamber such as a shaker are within the contemplation of the invention. In one preferred embodiment the dissolution chamber is moved end over end.

Generally, the apparatus will contain multiple dissolution chambers, buffer reservoirs, and collection reservoirs. One skilled in the art will recognize that the number of containers connected to the apparatus is limited only by the number of containers the connecting valves are able to efficiently interface with.

A principal object of the present invention is to provide an automated apparatus which in operation can carry out the testing of a sustained release product according to a predetermined program with a minimal amount of human supervision or manipulation. The present apparatus is able to simultaneously test several different sustained release products. While the apparatus can be constructed to test any number of samples simultaneously, the number six or twelve was found to be convenient in actual use.

A further object of the present invention is to provide an apparatus for testing a sustained release product which carries out the testing program under carefully controlled conditions giving reproducible data.

BRIEF DESCRIPTION OF THE DRAWINGS

Referring now to the drawings.

DESCRIPTION OF PREFERRED FORM OF INVENTION

Figure 1:
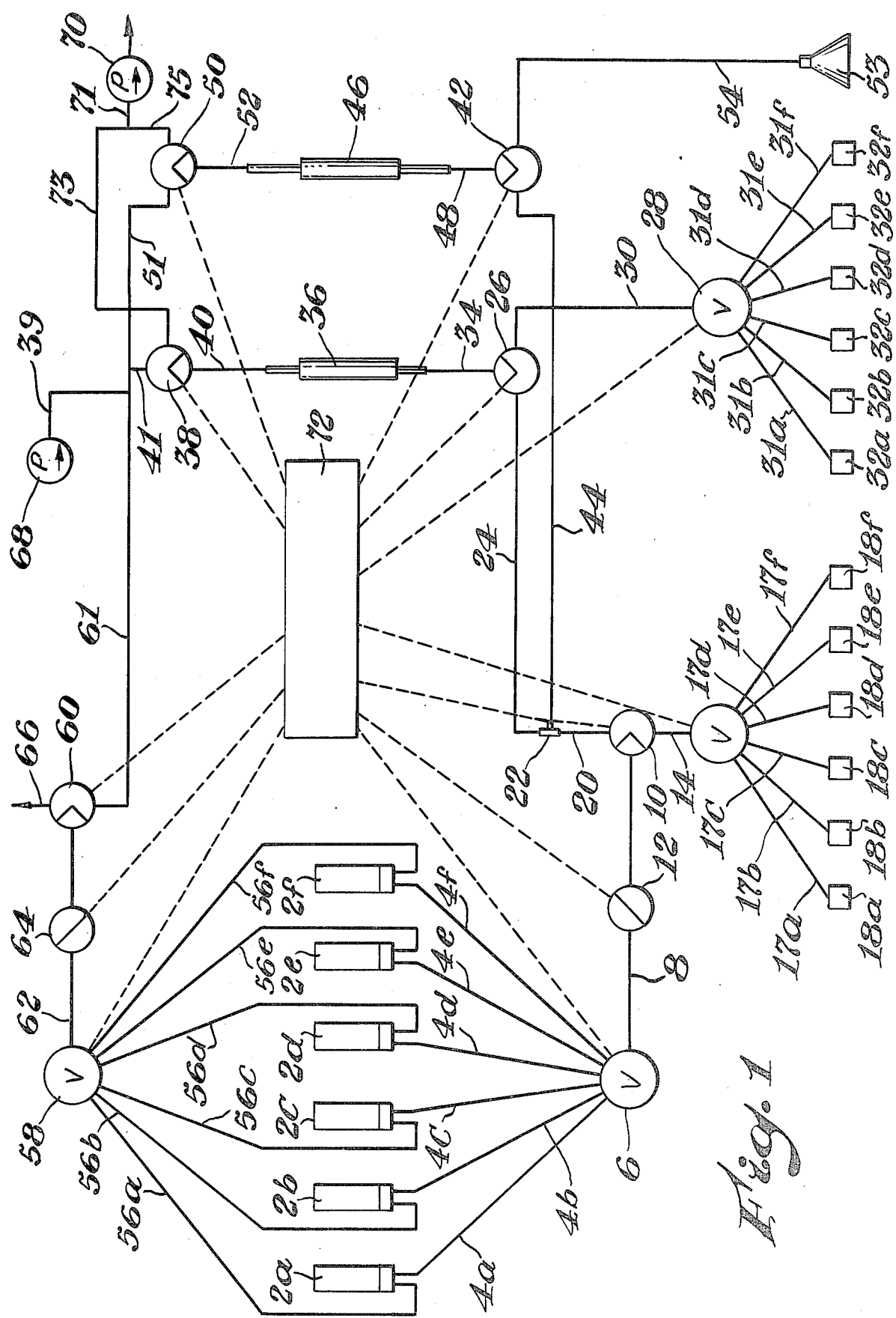
FIG. 1 is a schematic representation of the apparatus embodying the present invention.

Referring now to FIG. 1, which represents one preferred embodiment of the present invention, six dissolution chambers 2a, 2b, 2c, 2d, 2e and 2f are connected via separate fluid conduits 4a, 4b, 4c, 4d, 4e and 4f to a six-port valve 6 having a single output conduit 8 connected to one port of three-way valve 10. A two-way valve 12 is interposed in conduit 8 between six-port valve 6 and three-way valve 10. Fluid collection conduit 14 connects a second port of three-way valve 10 with the common port of six-port valve 16 which in turn selectively communicates through six separate conduits 17a, 17b, 17c, 17d, 17e and 17f with six fluid collection reservoirs 18a, 18b, 18c, 18d, 18e and 18f. The third port of three-way valve 10 is connected to one arm of tee connection 22 via a common conduit 20. A fluid conduit 24 connected to the second arm of tee connection 22 communicates with one port of a three-way valve 26. A second port of three-way valve 26 connects to the common port of six-port valve 28 via conduit 30. Six-port valve 28 selectively communicates through separate conduits 31a, 31b, 31c, 31d, 31e and 31f with six reservoirs 32a, 32b, 32c, 32d, 32e and 32f which during operation hold the pH buffer. The third port of the three-way valve 26 connects via conduit 34 to one end of pipet 36 for delivering measured amounts of pH buffer. In the specification and claims hereinafter pipet 36 may be referred to as buffer pipet. The buffer pipet 36 is connected at its opposite end to three-way valve 38 via conduit 40. The third arm of tee connection 22 communicates with three-way valve 42 via conduit 44. One end of a pipet 46 connects to the second port of three-way valve 42 via conduit 48. Pipet 46 during operation delivers measured amounts of a wash liquid; accordingly, pipet 46 will be referred to hereinafter as wash pipet. The opposite end of wash pipet 46 connects to three-way valve 50 via conduit 52. The third port of three-way valve 42 is connected to water reservoir 53 by conduit 54. The dissolution chambers 2a, 2b, 2c, 2d, 2e and 2f are also connected via separate venting tubes 56a, 56b, 56c, 56d, 56e and 56f to six-port valve 58. The common port of six-port valve 58 connects to three-way valve 60 via common vent tube 62. A two-way valve 64 is interposed intermediate between the common port of the six-port valve 58 and three-way valve 60 in common vent tube 62. A second port of three-way valve 60 connected to vent 66 provides access to the atmosphere. Air pump 68 connects to one port of each of three-way valves 38, 50 and 60 by means of manifold 39 connected to separate conduits 41, 51 and 61. Vacuum pump 70 connects to one port of three-way valves 38 and 50 by means of vacuum manifold 71 connected to separate conduits 73 and 75. The operation of valves 6, 10, 12, 16, 26, 28, 38, 42, 50, 58, 60 and 64 is sequentially controlled by timer and control unit 72, usually electrically operated, hereafter called the programmer as will be further explained below. The valves are designed such that at any one time any or all can be closed off or operating to provide connection between any two of the three conduits joined to the valves.

Figure 2:
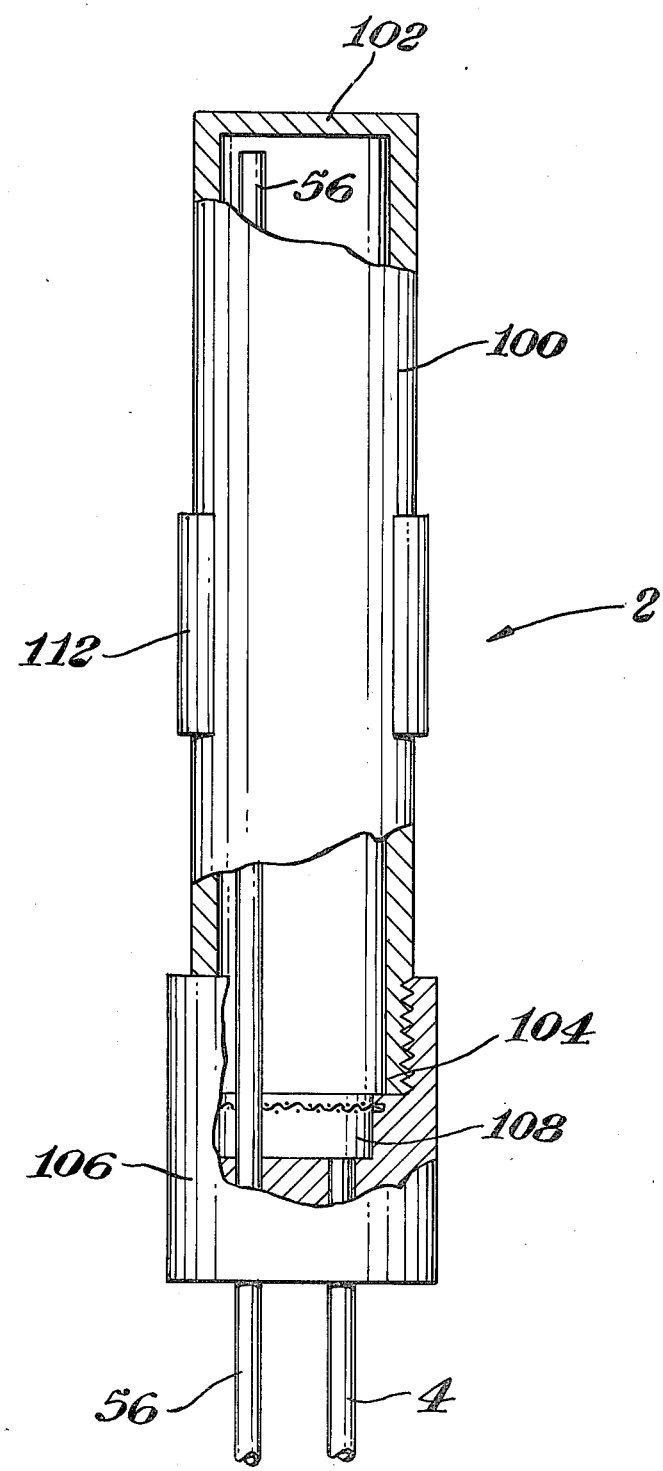
FIG. 2 is a vertical side elevation view, partially cut away, of one dissolution chamber.

Referring now to FIG. 2, a preferred embodiment of a dissolution chamber 2 comprises a hollow receptical 100 having a closed distal end 102 and an open proximal end 104. A closure member 106 is demountably engaged to proximal end 104 of receptical 100. Closure member 106 contains a cavity 108 into which opens a fluid conduit 4. Cavity 108 is defined at its upper end by screen 110 of a mesh size such that during operation, solid residues are prevented from entering cavity 108 from the hollow receptical 100 and being drawn into fluid conduit 4. A venting tube 56 extends through closure member 106 into hollow receptical 100 and terminates near distal end 102. The dissolution chamber 2 conveniently is held by a clamp assembly 112 of a conventional motor driven rack (not shown) which during operation reciprocally rotates the entire dissolution chamber about its center point whereby the distal end 102 and proximal end 104 circumscribe an arc of about 270 degrees.

In operation, a sustained release product intended for testing is placed in the hollow receptical 100, and the closure member 106 is then affixed. The fill cycle for the introduction of buffer into the dissolution chamber is accomplished by the formation of a first flow path connecting the dissolution chamber 2a and the first buffer reservoir 32a. Said flow path is formed when three-way valve 38 rotates to engage buffer pipet 36 to the vacuum line 73 and manifold 71 running to pump 70 and further upon the rotation of three-way valve 26 to form a communication between fluid conduits 34 and 30. Six-port valve 28 automatically selects the proper buffer from buffer reservoir 32a whereby buffer from said reservoir is drawn into buffer pipet 36 and said pipet is filled therewith. Valves 58, 64 and 60 also rotate to form communication between dissolution chamber 2a and vent 60 via common vent tube 62 and venting tube 56a. The measured buffer is introduced into the dissolution chamber 2a upon the rotation of valve 26 to form communication between buffer pipet 36 and the dissolution chamber via six-port valve 6. Upon engagement of buffer pipet 36 with air pump 68 via valve 38, line 41, and manifold 39 the measured buffer is forced into dissolution chamber 2a. Each dissolution chamber 2b, 2c, 2d, 2e, and 2f will be filled in succession in a like manner with buffer from reservoir 32a, the proper dissolution chamber being automatically selected by six-port valve 6.

Following the filling of all dissolution chambers, the rack holding the dissolution chambers is rotated for a predetermined period, e.g. about one hour, thereby agitating the contents of all the dissolution chambers. At the end of this period the used buffer is automatically removed, the dissolution chamber washed, and new buffer added. This operation requires an emptying cycle, a wash cycle and another fill cycle similar to the one already described, said cycles being carried out by a second flow path to empty the dissolution chamber of buffer, a third flow path to wash the dissolution chamber, and another first flow path as already described. The next buffer reservoir 32b is selected by six-port valve 28 and in the manner aready described buffer pipet 36 is filled with fresh buffer. Wash pipet 46 is filled with water by the rotation of three-way valve 42 to form communication between water reservoir 53 and pipet 46 via fluid conduits 54 and 48 while vacuum is engaged to wash pipet 46 by the rotation of three-way valve 50. The used buffer solvent already in the dissolution chamber 2a is forced out of the dissolution chamber into a preselected fluid collection reservoir 18a via the engagement of air pump 68 to the dissolution chamber by the selective rotation of valves 60, 64 and 58 to form a path therebetween, while communication between the dissolution chamber and fluid collection reservoir 18a is accomplished by the selective rotation of valves 6, 12, 10 and 16 to form a path of communication therebetween. The emptying cycle of the dissolution chamber takes place while the entire dissolution chamber is held substantially vertically with the distal end 102 uppermost.

The wash cycle takes place upon the rotation of three-way valves 42 and 10 to form a path of communication between wash pipet 46 and the dissolution chamber 2a. Valve 50 rotates to communicate air pump 68 via conduit 51 and manifold 39 with the path thus formed and the rinse water is forced into the dissolution chamber. The dissolution chamber 2a is emptied of rinse water upon the rotation of valves 10 and 16 to form communication between said dissolution chamber and fluid collection reservoir 18a via fluid collection conduit 14 and conduit 17a. The rinse is forced out of the dissolution chamber 2a by air pressure from pump 68 applied via manifold 39, conduit 61, conduit 62 and venting tube 59a, respectively. It has been found a second wash cycle substantially the same as the first may be desirable to thoroughly rinse the dissolution chamber of any residual buffer. The next buffer is introduced into the dissolution chamber upon the rotation of valve 26 to form communication between buffer pipet 36 and the dissolution chamber 2a. Upon engagement of buffer pipet 36 with air pump 68 via valve 38, the next buffer is forced into the dissolution chamber 2a. Each dissolution chamber is successively emptied, washed and refilled with fresh buffer in a like manner. The contents of the dissolution chambers are agitated for an additional period and the sequence begins again.

It will be seen that the sequence of operations for a complete fluid change requires three separate cycles: a fill cycle, an emptying cycle and a wash cycle.

In one preferred embodiment of the invention, valves 10, 12, 26, 38, 42, 50, 60 and 64 are electrically actuated valves. The six-port valves 6, 16, 28 and 58 are actuated by an electrically controlled pneumatic actuator system. The pneumatic actuator system is linked by mechanical means adapted to operate the six-port valves from one port to the next, as for example by use of a pawl and ratchet wheel linkage. Such systems are known in the art and are described in U.S. Pat. No. 3,802,272. Alternately, valves 10, 12, 26, 38, 42, 50, 60 and 64 can be pneumatic slider valves actuated by an electrically controlled pneumatic actuator system.

In one embodiment, the programmer uses a series of cam timers driven by synchronous motors. The rotating cam is in contact with a linear operated microswitch which is opened or closed by the movement of the cam.

Figure 3:
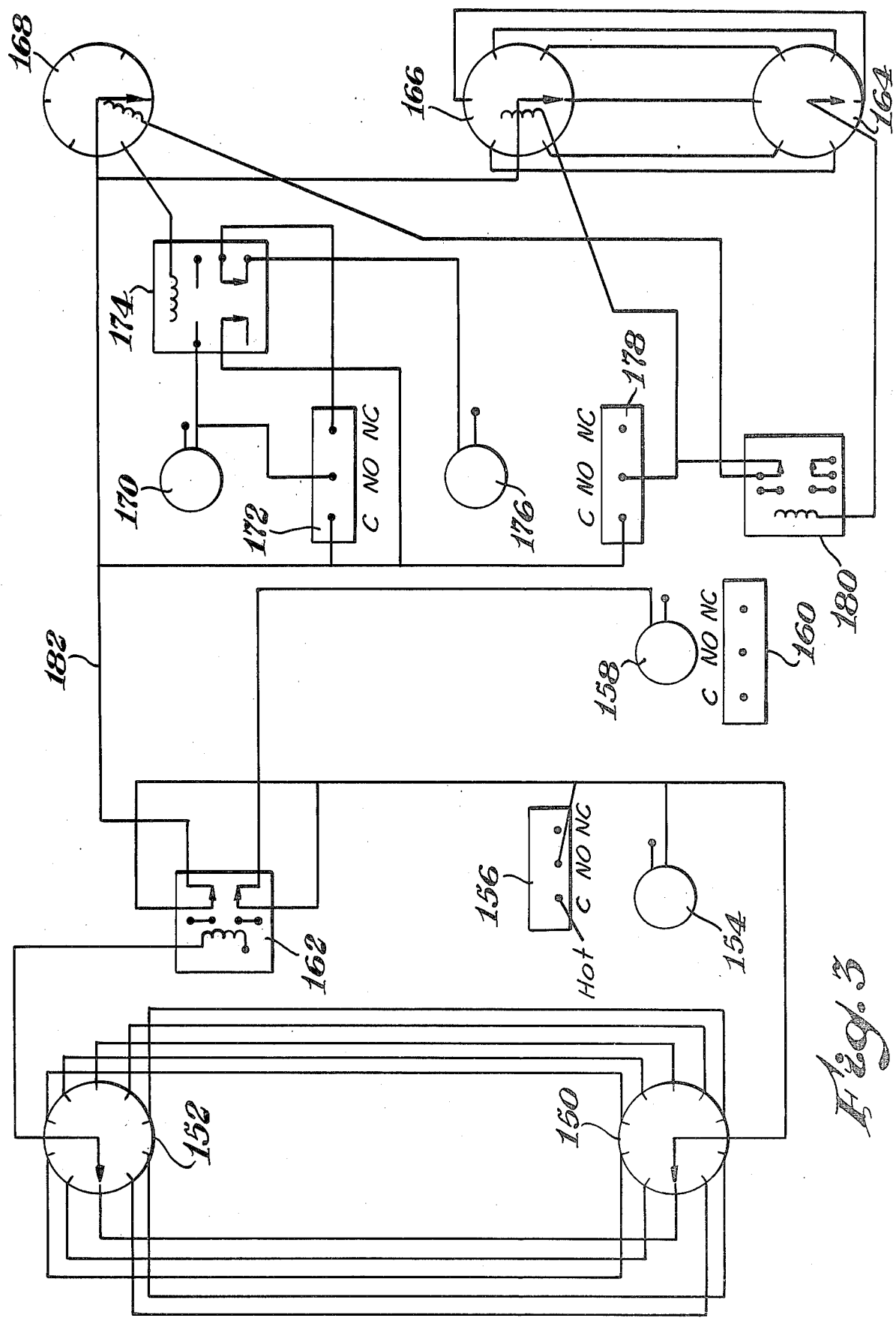
FIG. 3 is a simplified schematic representation of the method of operation of the programming means.

The microswitches in turn interface with various stepping switches, rotary switches and relays that coordinate the operation of the invention by selectively turning the cam motors on and off according to a preselected program of operation. A simplified schematic showing the manner in which the programmer selects the proper dissolution chamber for sampling and controls the total number of hours the analysis is to run is shown in FIG. 3.

The programmer consists of two interfacing systems. One system is for controlling the total number of hours the machine is to operate. A second system controls the actual movement of samples to and from the dissolution chambers. Resetting stepper switch 150 shows the elapsed hours, and the ten position rotary switch 152 shows the total hours the machine is to run. Motor 154 drives the ten-hour cam timer and activates the main power microswitch 156. Motor 158 drives a one-hour cam timer which controls stepping microswitch 160. Motor 158 for the one-hour cam timer is controlled through relay 162. Resetting stepper switch 150 is stepped by the operation of stepping microswitch 160 (interfacing connections are omitted for clarity).

Manual rotary switch 164 designates the number of dissolution chambers to be analyzed. Electrical rotary stepping switches 166 and 168 determine the dissolution chamber to be analyzed in the sequence. Motor 170 operates a one-hour cam timer which activates the main power microswitch 172 which also via relay 174 controls power to motor 176 for the one-minute cam timer. One-minute cam timer 176 activates stepping microswitch 178 which interfaces with relay 180.

In operation, ten position rotary switch 152 is manually set for the number of hours the machine is to run. Manual rotary switch 164 is set for the number of dissolution chambers to be analyzed. The one-hour cam timer 158 rotates once every hour activating stepping microswitch 160 which advances resetting stepper switch 150 one position. When resetting stepper switch 150 and ten position rotary switch 152 both are on the same position, relay 162 is activated which shuts off power to the one-hour cam timer 158 and all power from the ten-hour cam timer except for its motor 154. The ten-hour cam timer will continue to rotate until microswitch 156 shuts off its power.

The operation of the valves controlling the flow of liquids through the dissolution chambers is controlled by the rotary switch 164 and rotary stepping switches 166 and 168. Power for the operation of these switches is received from relay 162 via connection 182. One-hour cam timer 170 rotates once in one hour, and turns itself off via microswitch 172 at the completion of one revolution. The activation of microswitch 172 also turns one-minute cam timer 176 on. Every revolution of one-minute cam timer 176 advances rotary stepping switches 166 and 168 one position. When rotary stepping switches 166 and 168 are on the same position relay 180 is activated and stepping switch 166 is taken out of the stepping circuit. Simultaneously, relay 180 also cuts all power to the one-minute cam timer 176 except the motor, stepping microswitch 178, and the electrically operated valves which control the movement of liquids. The motor for the one-minute cam timer 176 will continue to rotate until stepping switch 168 is at position 6.

Position 6 of stepping switch 168 activates relay 174 and cuts power to the motor of cam timer 176. Simultaneously, power is given to the motor of one-hour cam timer 170 which will rotate until the next hourly interval. The operation of the valves themselves are controlled by an additional set of microswitches (not shown) actuated by a one minute cam timer which is shut off and turned on by relay 180.

One skilled in the art will appreciate that other programming means can be contemplated for activation of the various valves which control the flow of liquids through the machine.

We claim:
1. An apparatus for automatically testing sustained release drugs which comprises:
   (a) at least one dissolution chamber having means for circulating liquid therethrough;
   (b) agitating means contacting the contents of the dissolution chamber or moving the dissolution chamber itself during operation;
   (c) a first flow path contacting said dissolution chamber and a buffer reservoir;
   (d) a second flow path connecting said dissolution chamber and a fluid collection reservoir;
   (e) a third flow path connecting said dissolution chamber and a wash reservoir;
   (f) valving means for selectively activating and deactivating said first, second and third flow paths; and
   (g) programming means for selectively operating said valving means whereby said first, second and third flow path are sequentially activated and deactivated according to a preselected program.

2. The apparatus of claim 1 having a plurality of dissolution chambers connected via separate flow paths through valving means to said reservoirs for buffer, wash and fluid collection.

3. The apparatus of claim 1 comprising a plurality of dissolution chambers each having a vent connected through first valving means and a first conduit for the passage of liquid, wherein said first conduit connects to second valving means capable of sequentially forming a flow path for liquid between the dissolution chamber and a second common conduit selectively communicating with a plurality of fluid collection reservoirs by a third valving means; said third valving means capable of also forming a flow path between said second common conduit and a third conduit; said third conduit interfacing with means for alternately supplying measured quantities of a preselected buffer and rinse solution; means for measuring a preselected volume of buffer connecting to said third conduit; means for measuring a preselected volume of rinse solution also interfacing to said third conduit; a fourth valving means for alternately forming a flow path between said third conduit and said means for measuring a selected quantity of buffer and between said third conduit and means for measuring a selected quantity of rinse solution; means for moving liquids through said flow paths, thus formed by the activation of said second, third and fourth valving means and a programming means for coordinating the operation of all valving means thereby to selectively activate and inactivate the flow paths.

* * * * *